(12) United States Patent
Chav

(10) Patent No.: US 12,708,446 B2
(45) Date of Patent: Aug. 18, 2026

(54) COMPUTER-ASSISTED SURGERY WITH ELECTROMAGNETIC TRACKING

(71) Applicant: ORTHOSOFT ULC, Montreal (CA)

(72) Inventor: Ramnada Chav, Laval (CA)

(73) Assignee: ORTHOSOFT ULC, Montreal (CA)

( * ) Notice: Subject to any disclaimer, the term of this patent is extended or adjusted under 35 U.S.C. 154(b) by 707 days.

(21) Appl. No.: 17/089,117

(22) Filed: Nov. 4, 2020

(65) Prior Publication Data

US 2021/0128250 A1 May 6, 2021

Related U.S. Application Data

(60) Provisional application No. 62/930,259, filed on Nov. 4, 2019.

(51) Int. Cl.

| | |
|---|---|
| ***A61B 34/20*** | (2016.01) |
| ***A61B 17/56*** | (2006.01) |
| ***A61B 34/30*** | (2016.01) |
| ***A61B 90/00*** | (2016.01) |
| *A61B 17/00* | (2006.01) |

(52) U.S. Cl.

CPC .............. *A61B 34/20* (2016.02); *A61B 17/56* (2013.01); *A61B 34/30* (2016.02); *A61B 90/37* (2016.02); *A61B 2017/00119* (2013.01); *A61B 2017/564* (2013.01); *A61B 2034/2051* (2016.02); *A61B 2034/2061* (2016.02); *A61B 2034/2065* (2016.02); *A61B 2090/3916* (2016.02)

(58) Field of Classification Search

CPC .......... A61B 34/20; A61B 34/30; A61B 17/56

See application file for complete search history.

(56) References Cited

U.S. PATENT DOCUMENTS

| | | | |
|---|---|---|---|
| 6,762,600 B2 | 7/2004 | Khalfin | |
| 7,657,298 B2 | 2/2010 | Moctezuma de la Barrera et al. | |
| 10,292,774 B2 | 5/2019 | McDonell | |
| 2011/0152676 A1* | 6/2011 | Groszmann | A61B 6/12 600/426 |
| 2012/0316486 A1* | 12/2012 | Cheung | G01S 17/06 342/450 |
| 2019/0029759 A1* | 1/2019 | Mcdonell | A61B 34/20 |

* cited by examiner

*Primary Examiner* — Sameh R Boles

(74) *Attorney, Agent, or Firm* — NORTON ROSE FULBRIGHT CANADA LLP

(57) ABSTRACT

There is described a system for tracking at least one tool relative to a bone in computer-assisted surgery. The system generally has a processing unit; and a non-transitory computer-readable memory communicatively coupled to the processing unit and comprising computer-readable program instructions executable by the processing unit for: continuously emitting an electromagnetic field in a surgical volume incorporating at least one electromagnetic sensor on a bone and/or tool; continuously receiving a signal indicative of a position and/or orientation of the electromagnetic sensor relative to the emitting of electromagnetic field; processing the signal to determine the position and/or orientation of the at least one electromagnetic sensor; obtaining geometrical data relating the at least one electromagnetic sensor to the bone and/or tool; and continuously tracking and outputting a first position and/or orientation of the bone and/or tool using the geometrical data and the position and/or orientation of the at least one electromagnetic sensor.

19 Claims, 6 Drawing Sheets

EM TRACKING CONTROLLER
ROBOTIZED SURGERY CONTROLLER

COMPUTER-ASSISTED SURGERY WITH ELECTROMAGNETIC TRACKING

CROSS-REFERENCE TO RELATED APPLICATION

The application claims the priority of U.S. Patent Application No. 62/930,259, filed on Nov. 4, 2019, and incorporated herein by reference.

TECHNICAL FIELD

The present application relates to bone and tool tracking in computer-assisted orthopedic surgery, such as in robotized computer-assisted surgery.

BACKGROUND OF THE ART

Tracking of surgical instruments or tools is an integral part of computer-assisted surgery (hereinafter "CAS"). The tools are tracked for position and/or orientation in such a way that information pertaining to bodily parts is obtained. The information is then used in various interventions (e.g., orthopedic surgery, neurological surgery) with respect to the body, such as bone alterations, implant positioning, incisions and the like during surgery.

The tracking technologies may use different technologies, such as mechanical, acoustical, magnetic, optical and radio frequency (RF) tracking. Depending on the technology used, different types of trackable members are fixed, permanently or temporarily, to the item that needs to be tracked. For instance, during Total Knee Replacement (TKR) surgery, trackable members are fixed to the limbs and to the different surgical instruments, and these trackable members are tracked by the tracking system. The CAS system calculates position and orientation data associated with the tracking, and the information displayed by the computer is used by the surgeon to visualize the position of the instrument(s) being manipulated with respect to the limbs, or in numerical values.

Optical tracking is commonly used in different forms. For example, passive retroreflective components are provided on tools and bones. In order to obtain values for position and/or orientation, the optical elements must be in the line of sight of the optical sensor device. The requirement for a line of sight between image acquisition devices and the objects is a common constraint with optical tracking systems. For example, surgery employing optical tracking may be imposed a given orientation as a function of the required visibility between the optical sensor apparatus and the optical elements. If the line of sight is disrupted, orthopedic tracking may be paused, as a possible consequence.

SUMMARY

In accordance with a first aspect of the present disclosure, there is provided a system for tracking at least one tool relative to a bone in computer-assisted surgery, comprising: a processing unit; and a non-transitory computer-readable memory communicatively coupled to the processing unit and comprising computer-readable program instructions executable by the processing unit for: continuously emitting an electromagnetic field in a surgical volume incorporating at least one electromagnetic sensor on a bone and/or tool; continuously receiving a signal indicative of a position and/or orientation of the electromagnetic sensor relative to the emitting of electromagnetic field; processing the signal to determine the position and/or orientation of the at least one electromagnetic sensor; obtaining geometrical data relating the at least one electromagnetic sensor to the bone and/or tool; and continuously tracking and outputting a first position and/or orientation of the bone and/or tool using the geometrical data and the position and/or orientation of the at least one electromagnetic sensor.

Further in accordance with the first aspect of the present disclosure, continuously emitting can for example include continuously emitting electromagnetic fields of different frequencies.

Still further in accordance with the first aspect of the present disclosure, the outputting can for example include imaging the bone and/or tool.

Still further in accordance with the first aspect of the present disclosure, the method can for example further comprise moving a robot arm based on the outputting of the first position and/or orientation of the bone and/or tool.

Still further in accordance with the first aspect of the present disclosure, the method can for example further comprise, using an optical waveguide modeling system having at least one multicore optical fiber with at least one portion attached to the bone and/or tool, generating a waveguide model representing the multicore optical fiber as attached to the bone and/or tool; and continuously tracking and outputting a second position and/or orientation of the bone and/or tool using the waveguide model.

Still further in accordance with the first aspect of the present disclosure, the method can for example further comprise comparing the first position and/or orientation of the bone and/or tool to the second position and/or orientation of the bone and/or tool.

Still further in accordance with the first aspect of the present disclosure, the method can for example further comprise generating an alert upon determining a difference exceeding a threshold between the first and second positions and/or orientations of the bone and/or tool.

In accordance with a second aspect of the present disclosure, there is provided a system for tracking at least one bone in computer-assisted surgery, comprising: at least one electromagnetic source; at least one electromagnetic sensor configured to be secured to a bone and/or a tool; and a computer-assisted surgery controller for continuously driving the electromagnetic source to emit an electromagnetic field in a surgical volume incorporating the at least one electromagnetic sensor; continuously receiving a signal indicative of a position and/or orientation of the electromagnetic sensor relative to the emitting of electromagnetic field; processing the signal to determine the position and/or orientation of the at least one electromagnetic sensor; obtaining geometrical data relating the at least one electromagnetic sensor to the bone and/or tool; and continuously tracking and outputting a first position and/or orientation of the bone and/or tool using the geometrical data and the position and/or orientation of the at least one electromagnetic sensor.

Further in accordance with the second aspect of the present disclosure, the system can for example further comprise continuously displaying the first position and/or orientation of the bone and/or tool on a display screen.

Still further in accordance with the second aspect of the present disclosure, the system can for example further comprise a robot arm moved based on the first position and/or orientation of the bone and/or tool.

Still further in accordance with the second aspect of the present disclosure, the system can for example further comprise an optical waveguide modeling system having at least one multicore optical fiber with at least one portion attached to the bone and/or tool, the computer-assisted surgery controller generating a waveguide model representing the multicore optical fiber as attached to the bone and/or tool; and continuously tracking and outputting a second position and/or orientation of the bone and/or tool using the waveguide model.

Still further in accordance with the second aspect of the present disclosure, the computer-assisted surgery controller can for example compare the first position and/or orientation of the bone and/or tool to the second position and/or orientation of the bone and/or tool.

Still further in accordance with the second aspect of the present disclosure, the computer-assisted surgery controller can for example generate an alert upon determining a difference exceeding a threshold between the first and second positions and/or orientations of the bone and/or tool.

Still further in accordance with the second aspect of the present disclosure, the system can for example further comprise an indicator indicating the alert within the surgical volume.

In accordance with a third aspect of the present disclosure, there is provided a method for tracking a bone and/or tool in computer-assisted surgery, comprising: continuously emitting an electromagnetic field in a surgical volume incorporating at least one electromagnetic sensor on a bone and/or tool; continuously receiving a signal indicative of a position and/or orientation of the electromagnetic sensor relative to the emitting of electromagnetic field; processing the signal to determine the position and/or orientation of the at least one electromagnetic sensor; obtaining geometrical data relating the at least one electromagnetic sensor to the bone and/or tool; and continuously tracking and outputting a first position and/or orientation of the bone and/or tool using the geometrical data and the position and/or orientation of the at least one electromagnetic sensor.

Further in accordance with the third aspect of the present disclosure, continuously emitting can for example include continuously emitting electromagnetic fields of different frequencies.

Still further in accordance with the third aspect of the present disclosure, the outputting can for example further include imaging the bone and/or tool.

Still further in accordance with the third aspect of the present disclosure, the method can for example further comprise, using an optical waveguide modeling system having at least one multicore optical fiber with at least one portion attached to the bone and/or tool, generating a waveguide model representing the multicore optical fiber as attached to the bone and/or tool; and continuously tracking and outputting a second position and/or orientation of the bone and/or tool using the waveguide model.

Still further in accordance with the third aspect of the present disclosure, the method can for example further comprise comparing the first position and/or orientation of the bone and/or tool to the second position and/or orientation of the bone and/or tool.

Still further in accordance with the third aspect of the present disclosure, the method can for example further comprise generating an alert upon determining a difference exceeding a threshold between the first and second positions and/or orientations of the bone and/or tool.

DETAILED DESCRIPTION

Figure 1:
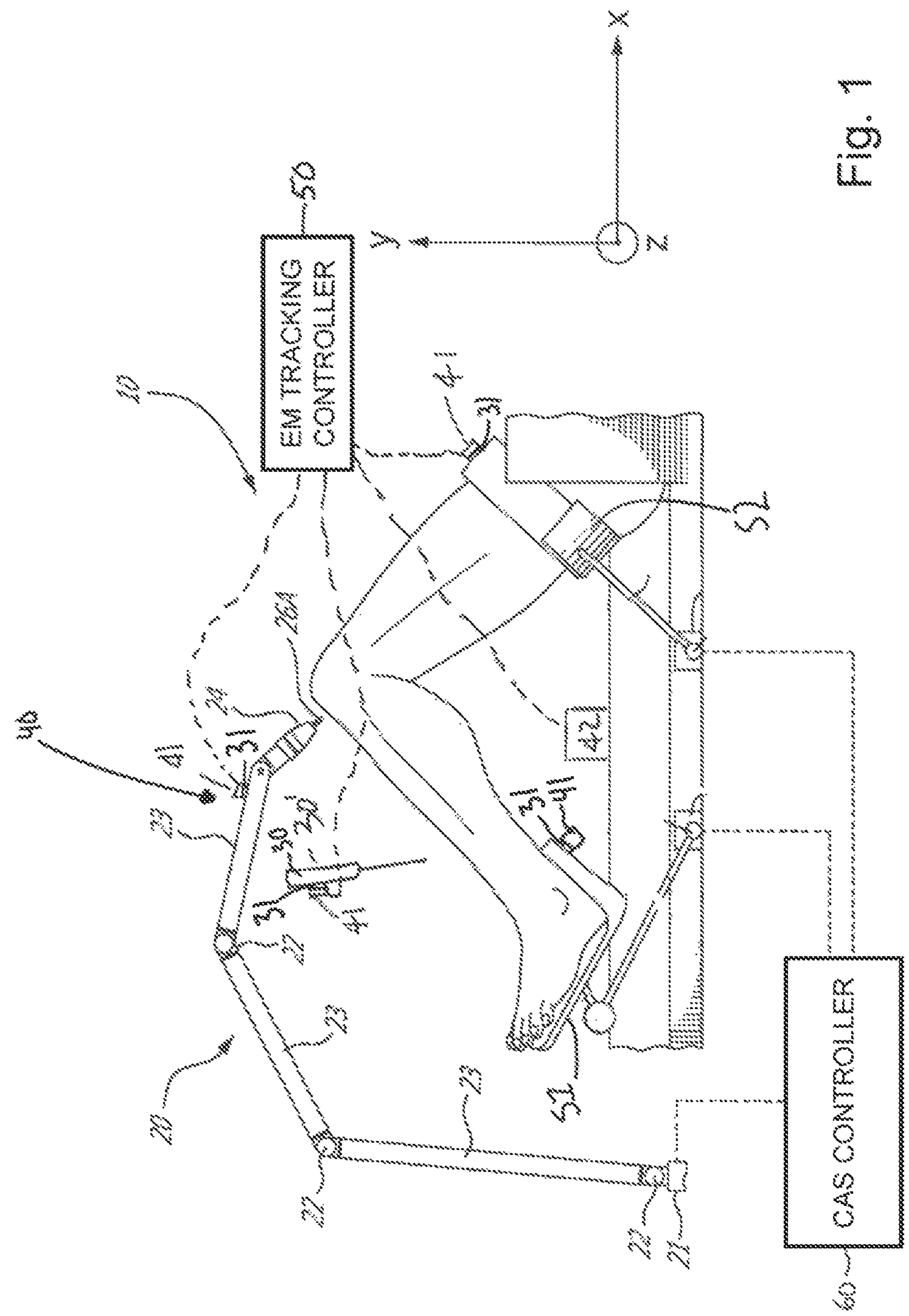
FIG. 1 is a schematic view of a computer-assisted surgery (CAS) system with an example electromagnetic tracking set used with a robotic system, in accordance with one or more embodiments.
Figure 2:
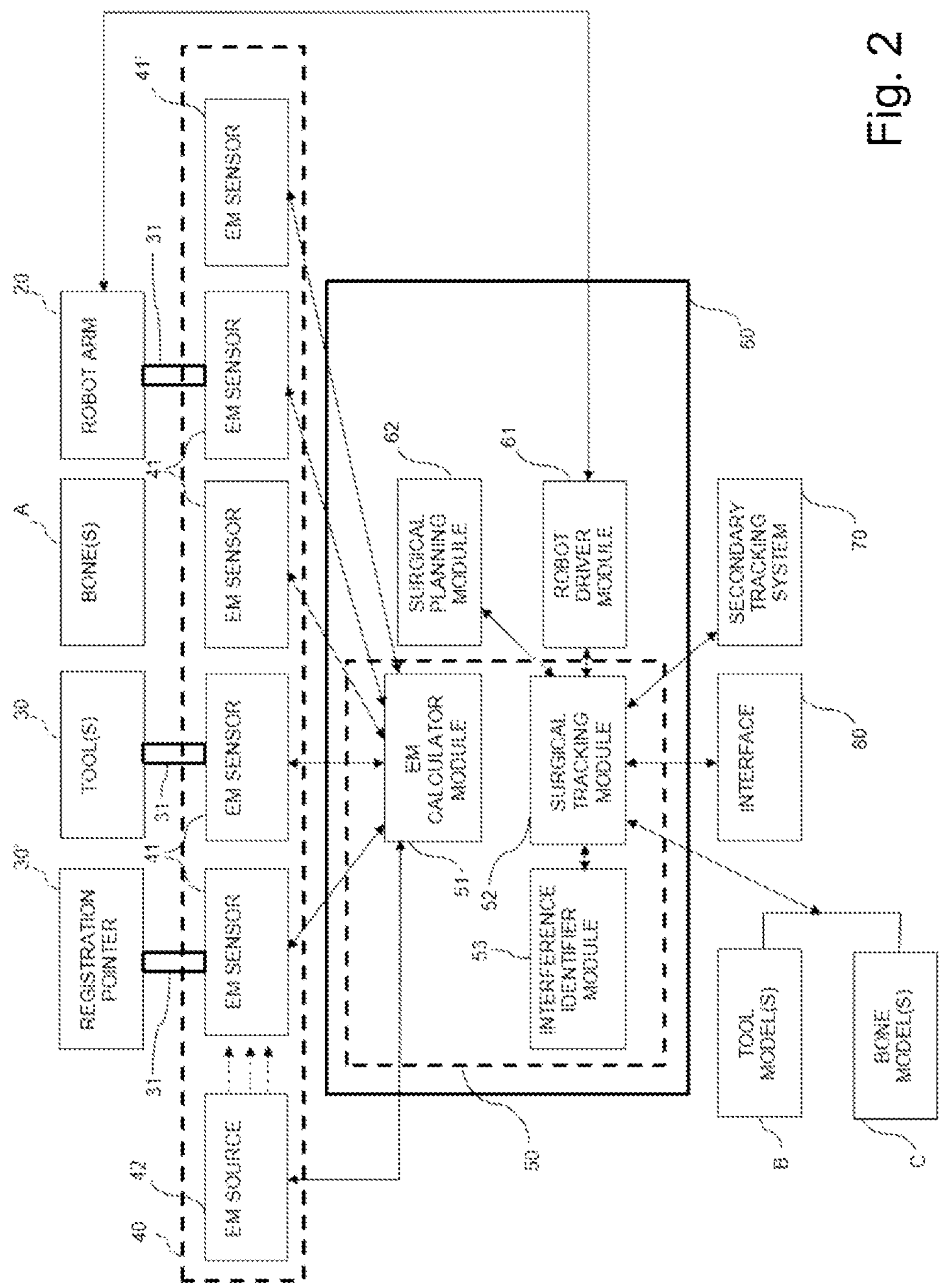
FIG. 2 is a block diagram of a CAS controller and tracking controller with the automated robotic CAS system of FIG. 1, in accordance with one or more embodiments.

Referring to the drawings and more particularly to FIGS. 1 and 2, a computer-assisted surgery (CAS) system is generally shown at 10, and is used to perform orthopedic surgery maneuvers on a patient, including pre-operative analysis of range of motion and implant assessment planning, as described hereinafter. The system 10 is shown relative to a patient's knee joint in supine decubitus, but only as an example. The system 10 could be used for other body parts, including non-exhaustively hip joint, spine, and shoulder bones, with the patient in other positions.

The CAS system 10 may be used in robotized surgery, and may consequently have a robot arm 20. The system 10 may also or alternatively be used in free-hand mode by a human operator, and may consequently have surgical tools such as those shown at 30. The CAS system 10 may further have an electromagnetic (EM) tracking set 40, an EM tracking controller 50, and a CAS controller 60. A secondary tracking system 70 and an interface 80 may also be present.

- If present, the robot arm 20 is the working end of the CAS system 10, and is used to perform bone alterations as planned by an operator and/or the CAS controller 60 and as controlled by the CAS controller 60. The robot arm 20 may also be configured for collaborative/cooperative mode in which the operator may manipulate the robot arm 20. For example, the tooling end, also known as end effector, may be manipulated by the operator;
- If used in a free-hand mode or in collaborative/cooperation mode, tools 30 may be part of the CAS system 10. Each of the tools 30 performs a given function related to computer-assisted surgery, such as altering a bone or organ, navigating, calibrating, etc;
- The EM tracking set 40 includes one or more EM sensors 41 and one or more EM source(s) 42, that are used for electromagnetic tracking;
- The EM tracking controller 50 operates the EM tracking set 40, and is tasked with determining the position and/or orientation of the various relevant objects during the surgery procedure, such as the bone(s), organ(s) and tool(s), using data acquired by the tracking set 40 for navigation in a coordinate system (also known as frame of reference, global reference system, etc);

- The CAS controller 60 controls the robot arm 20 for instance using the position and/or orientation produced by the EM tracking controller 50. Moreover, as described hereinafter, the CAS controller 60 may also drive the robot arm 20 through a planned surgical procedure;
- The secondary tracking system 70 may optionally be used to track the bones of the patient and/or the robot arm 20. For example, the secondary tracking system 70 may assist output redundant tracking information to confirm the navigation data from the EM tracking controller 50. An example of such secondary tracking can include, but is not limited to, an optical waveguide modeling system such as the one described with reference to FIG. 4;
- The interface 80 may take various forms and outputs and communicates navigational data to the operator of the CAS system 10.

Referring back to FIG. 1, a schematic example of the robot arm 20 is provided. The robot arm 20 may stand from a base 21, for instance in a fixed relation relative to the operating-room (OR) table supporting the patient, whether it is attached or detached from the table. The relative positioning of the robot arm 20 with respect to the patient is a determinative factor in the precision of the surgical procedure, whereby a foot support S1 and thigh support S2 may assist in keeping the operated limb fixed in the illustrated X, Y, Z coordinate system. Although not shown, the foot support S1 and/or the thigh support S2 could be automated to robotize the displacement and positioning of the patient's leg, and optionally to perform tests on the leg. The robot arm 20 has a plurality of joints 22 and links 23, of any appropriate form, to support a tool head 24 that interfaces with the patient. For example, the end effector or tool head 24 may optionally incorporate a force/torque sensor for collaborative/cooperative control mode, in which an operator manipulates the robot arm 20. The robot arm 20 is shown being a serial mechanism, arranged for the tool head 24 to be displaceable in a desired number of degrees of freedom (DOF). For example, the robot arm 20 controls 6-DOF movements of the tool head 24, i.e., X, Y, Z in the coordinate system, and pitch, roll and yaw. Fewer or additional DOFs may be present. For simplicity, only a generic illustration of the joints 22 and links 23 is provided, but more joints of different types may be present to move the tool head 24 in the manner described above. The joints 22 are powered for the robot arm 20 to move as controlled by the CAS controller 60 in the six DOFs, and in such a way that the position and orientation of the tool head 24 in the coordinate system may be known, for instance by readings from encoders on the various joints 22. As described below, such encoders may be part of or operated by a secondary tracking system 70. Therefore, the powering of the joints 22 is such that the tool head 24 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, and incorporated herein by reference. The position and orientation of the tool head 24 may be calculated using solely the encoders on the various joints. The tracking set 40 and/or secondary tracking system 70 may also be used for this purpose, or other systems such as inertial sensor systems. It may be necessary to have the base 21 of the robot arm 20 fixed in a known location relative to the robot arm 20 or alternatively be marked with a tracking pattern compatible with the secondary tracking system 70.

In FIG. 1, the tool head 24 supports a burr 26A, used to resurface or drill a bone. The tool head 24 may also comprise a chuck or like tool interface, typically actuatable in rotation. The tool head 24 may have laminar spreader plates, actuatable independently from a remainder of the tool head 24, for simultaneous use with a tool support by the tool head 24. The laminar spreader plates are used to spread soft tissue apart to expose the operation site. The laminar spreader plates may also be used as pincers, to grasp objects, etc. As a non-exhaustive example, other tools that may be supported by the tool head 24 include a registration pointer, a reamer (e.g., cylindrical, tapered), a reciprocating saw, a retractor, a laser rangefinder or light-emitting device (e.g., the indicator device of U.S. Pat. No. 8,882,777) depending on the nature of the surgery. The various tools may be part of a multi-mandible configuration or may be interchangeable, whether with human assistance, or as an automated process. The installation of a tool in the tool head 24 may then require some calibration in order to track the installed tool in the X, Y, Z coordinate system of the robot arm 20.

Referring to FIGS. 1 and 2, the tools 30 may be of any appropriate kind, depending on the type of surgery, and may include reamers, rasps, saws, cutting blocks, cut guides, tracker bases, drills, catheters, impactors, to name a few. Each of the tools 30 performs a given function related to computer-assisted surgery. For instance, some tools perform alterations on a bone or organ, such a reamers, rasps, saws, drills. Another contemplated function is to assist in computer-assisted navigation, i.e., tracking the relative position and/or orientation of bones and tools, such as in the coordinate system X, Y, Z. A registration pointer is shown as 30' in FIGS. 1 and 2, and is one of the tools 30 that may be used for navigation, as are cut guides, impactors, tracker bases, validation devices, etc. Some tools may be used to assist in positioning an implant, such as an impactor. Those tools may be regarded as contributing to the navigation.

One or more mounts 31 may be provided on at least some of the tools 30, the robot arm 20, foot and/or thigh supports 51 and S2, for receiving the EM sensors 41 in a known and repeatable manner. Such mounts 31 may also be standalone units (i.e., not on a tool 30), with such mounts 31 being configured to be secured to bones A, organs and the like. For example, such mounts 31 may be as described as a support, connecting dock and/or connection device in U.S. Pat. No. 9,801,685, incorporated herein by reference.

Still referring to FIGS. 1 and 2, the EM tracking set 40 includes one or more EM sensor(s) 41 and one or more EM source(s) 42, that are used for electromagnetic tracking. According to some embodiments, the EM tracking set 40 uses tuned AC electromagnetic technology for the tracking of the EM sensors 41 in position and orientation relative to a referential space, such as the X, Y, Z coordinate system.

In one embodiment, each of the tools 30 has a dedicated EM sensor 41 (i.e., one per tool 30), and one or more bones and/or organs may also have a dedicated EM sensor 41. A given EM sensor 41 may be used sequentially with a first tool 30 and then a second tool 30 after the task with the first tool 30 is completed. Calibration steps and/or interactions with the EM tracking controller 50 may be required in transitioning one of the EM sensors 41 from one tool to another.

Each sensor 41 has coil(s) to detect a magnetic flux resulting from a electromagnetic field produced by the EM source(s) 42. In an embodiment, one or more of the EM sensors 41 has three non-parallel sensor coils that, when paired with a given EM source 42, may produce position and/or orientation tracking in a referential system including the EM source 42. The tracking may be for both position and orientation, i.e., six degrees of freedom, X, Y, Z in a coordinate system, and pitch, roll and yaw. Fewer or additional DOFs may be tracked. The EM sensors 41 may include different types of sensor components, such as solid-state sensors, quantum, or flux gage sensors. In an embodiment, the solid-state sensors implement giant magnetoresistance (GMR). The sensors 41 may also include superconducting quantum interference device (SQUID) magnetometers and the like.

The EM sensors 41 may be applied directly against the objects (e.g., robot arm 20, tools 30 and/or bones A). The EM sensors 41 employing the afore-mentioned technologies may be relatively small in size, e.g., in the range of millimeters, and can be secured non-invasively to bones, and soft tissue. Any appropriate type of securing means may be used, including staples, adhesives, among others. The positioning of such small-size EM sensors 41 on bones A and tools 30 may be random, provided the EM sensors 41 are fixed to the object.

In another embodiment, the EM sensors 41 have their electronic components (e.g., coils and/or circuitry) embedded in a casing, cable or the like. The EM sensors 41 may optionally be calibrated, in that a geometry of the casing may be known along with location of the sensor components inside the casing. For example, such casings may be as described as those of navigation units in U.S. Pat. No. 9,801,685, incorporated herein by reference. Therefore, as described below, a calibration of the CAS system 10 may be facilitated by the use of a calibrated casing for the EM sensors 41, even though optional. The casings therefore are a complementary feature of the mount, and are illustrated jointly by 31 in FIGS. 1 and 2. The wires of the EM sensors 41 may be covered by sheaths that form EM shields to isolate the wires from ambient interference.

The EM source 42 is an EM transmitter, emitting an electromagnetic field, such as an electromagnetic dipole field. In an embodiment, the EM source 42 produces a modulated AC electromagnetic field (modulated waveform), with the AC electromagnetic field having induction-vector components that will be detected and measured using the EM sensors 41. The EM source 42 may have source coils to produce the electromagnetic field. In an embodiment, there are three source coils in the EM source 42, arranged in a non-parallel manner, for the 6-DOF tracking, and electronic circuitry to control the generation of the electromagnetic field. For instance, the electronic circuitry may control the magnitude and phase of the modulated electromagnetic field. Further, the EM source 42 may produce an electromagnetic field with a modulation frequency that is close to the frequency of the EM sensors 41. The EM source 42 may for instance emit a single-tone signal, with amplitude or frequency modulation.

The EM source 42 may be positioned in a fixed manner in relatively close proximity to the surgical volume, so as to be close to the EM sensors 41, and hence avoid interference from larger metallic objects. Consequently, the location of the EM source 42 is fixed in the referential system, and may therefore designate the origin of the referential system. In an embodiment, the origin may be arbitrarily positioned. In some embodiments, more than one EM source 42 are configured to emit respective electromagnetic fields of different frequencies. In these embodiments, the EM sensors 41 may be configured to sense and discriminate the electromagnetic fields carrying the different frequencies. In some embodiments, a first set of EM sensors 41 are configured to sense the electromagnetic field of a first frequency whereas a second set of EM sensors 41 are configured to sense the electromagnetic of a second frequency different from the first frequency, and so forth for different frequencies if need be. Such redundancy may be useful for confirming the tracking of tool(s) 30, bone(s) A and/or organ(s) in quasi real time.

Referring to FIG. 2, the EM tracking controller 50 may be part of any suitable processor unit, such as a personal computer or computers including laptops and desktops, tablets, server, etc. The EM tracking controller 50 runs various modules, in the form of algorithms, code, non-transient executable instructions, etc, in order to track the robot arm 20, tools 30 and/or bones or organs A in the manner described herein. The EM tracking controller 50 may be a subpart of the CAS controller 60, or an independent unit. The tracking controller 50 operates the tracking set 40, so as to receive and process signals from the EM tracking set 40 to compute position and/or orientation data, i.e., to determine the relative position of the objects.

The EM tracking controller 50 may have an EM calculator module 51, to process the signals and determine the position and orientation of the EM sensors 41 as a function of the signal from the EM source 42. Though not shown in FIG. 2, the EM calculator module 51 may be a standalone unit, to which the EM sensors 41 and the EM source 42 are wired and/or in wireless communication therewith. Each of the EM sensors 41 and EM source 42 may for example have a dedicated channel and/or port in the standalone EM calculator module unit. The EM calculator module 51 may therefore transmit tracking data for each EM sensor 41 to a surgical tracking module 52 of the EM tracking controller 50.

The surgical tracking module 52 is tasked with converting sensor tracking data into position and/or orientation tracking data for the objects involved in surgery. As a first step, for instance, the surgical tracking module 52 of the tracking controller 50 may associate the EM sensors 41 to the various objects of the surgical procedure, in the referential system. Different approaches may be taken to achieve the association. In an embodiment, the EM tracking controller 50 (e.g., via the interface 80) prompts the operator to perform identifying actions, such as moving the tools 30 with EM sensors 41 one after the other. In another embodiment, each EM sensor 41 is pre-identified or pre-connected to objects. In yet another embodiment, the surgical flow of the procedure incorporates tool identifying steps, and placement of EM sensors 41 on the bone(s) or organ(s) A with operator guidance and/or entry steps. For example, the registration pointer 30' may be one of the first tools to be used, to obtain points on a bone A, to identify other tools 30 equipped with EM sensors 41, or to digitize features on the tools (e.g., cut plane, rotational axes) or bones. As the operator is requested to manipulate the registration pointer 30', the surgical tracking module 52 may identify movements of one of the EM sensors 41 as being that of the EM sensor 41 on the registration pointer 30'. Accordingly, the EM sensors 41 are paired to an object, such as robot arm 20, tool(s) 30 and/or bone(s) A.

The surgical tracking module 52 may then obtain geometrical data for the robot arm 20, tool(s) 30 and/or bone(s) A, so as to convert sensor tracking data into position and/or orientation tracking data for the objects involved in surgery. Again, different alternative or complementary approaches may be taken to obtain the geometrical data. In an embodiment, a calibration device such as one described in U.S. Pat. No. 6,996,487, incorporated herein by reference, may be used to determine the position of working ends of the robot arm 20 and/or tool(s) 30 in the referential system. Similar procedures may be performed to correlate the robot arm 20 and/or tool(s) 30 to known positions.

In an embodiment, the surgical tracking module 52 may be provided with or may access models of the objects to be tracked, such as tool models B and bone models C. The virtual tool models B may be provided by the tool manufacturer, or may also be generated in any appropriate way so as to be a virtual 3D representation of the tool(s) 30. Additional data may also be available, such as tool orientation (e.g., axis data and geometry). The tool models B may be used in conjunction with calibration devices or techniques, to locate the tool(s) 30 in the referential system through their associated EM sensors 41, and to then merge the tool model B to the associated EM sensor 41. In another embodiment, in which the geometrical relation of a coupling between a casing of the EM sensor 41 and a mount 31 on the tool 30 is known, the surgical tracking module 52 may merge the tool model B to the associated EM sensor 41 using the predetermined and programmed geometrical relation. The merge may optionally be validated, for instance using a calibration device, or the registration points 30'.

The bone models C may optionally be used to provide additional bone data to the tracking of the bones A with the EM sensors 41. However, the presence of EM sensors 41 on bones may not be necessary. Indeed, if the bone(s) and the EM source 42 are fixed in the referential system, surface points on the bones may be given fixed X,Y,Z coordinates that remain fixed through the procedure. The bone models may be acquired from pre-operative imaging (e.g., MRI, CT-scans), for example in 3D or in multiple 2D views, including with 2D X-ray to 3D bone model technologies. The virtual bone models C may also include some image processing done preoperatively, for example to remove soft tissue or smoothen the surfaces that will be exposed and tracked. The virtual bone models C may be of greater resolution at the parts of the bone that will be tracked during surgery, such as the knee articulation in knee surgery. The bone models C may also carry additional orientation data, such as various axes (e.g., longitudinal axis, mechanical axis, etc). The bone models C may therefore be patient specific. It is also considered to obtain bone models from a bone model library, with generated 3D surface of the bone obtained from bone landmark registration (e.g., with the robot arm 20 or with the registration pointer 30') matched with a corresponding bone surface from the bone atlas. An operator may be guided in digitizing specific detectable landmarks on the bone(s) to ensure the detectable landmarks are part of the modeled surface for subsequent matching. In matching the 3D geometry to the bone models C, the surgical tracking module 52 may reduce its computation using different strategies. According to one possibility, a surgical planning module 62 may provide some guidance as to parts of the bones that are altered during the surgical procedure. Likewise, the bone model(s) C may have higher resolution for the parts of the bone that will be altered during surgery. The remainder of the bone may be limited to information on landmarks, such as axis orientation, center of rotation, midpoints, etc. A similar approach may be taken for the tool models B, with the focus and higher detail resolution being on parts of the tools that come into contact with the bone.

Therefore, after such calibration and/or set-up steps, the surgical tracking module 52 may generate and/or track a 3D geometry of objects from the EM tracking, using registered landmark points on the bones or organs. For instance, the surgical tracking module 52 can generate a 3D model of a bone surface using points from the tracked registration pointer 30' equipped with one of the EM sensors 41. In an embodiment, the surgical tracking module 52 may, using the virtual models C of the bone(s), match the 3D geometry with the virtual models C, with the objects detected being segmented. Consequently, the tracking controller 50 may determine a spatial relationship between an object being tracked and the preoperative 3D model of the object, to provide a dynamic (e.g. real time or quasi real time) intraoperative tracking of the bones relative to the tools. The tracking set 40 may continuously capture movements of the objects, for the tracking controller 50 to perform a continuous tracking of the objects.

The EM tracking controller 50 may have an interference identifier module 53. The interference identifier module 53 may detect when interference and/or distortion occurs in the tracking set 40. The interference may be of temporary nature, such as the presence of an interfering object, or may be of permanent nature, such as proximity to sizable metallic objects near the EM sensors 41 and/or EM source(s) 42. The interference identifier module 53 may determine the nature of the interference, for example by obtaining the readings of an undedicated EM sensor 41' at a known distance from the EM source 42. As a result of the identification of interference by the interference identifier module 53, the EM tracking controller 50 may signal an interference to the operator of the CAS system 10 via the interface 80.

Therefore, the tracking controller 50 continuously updates the position and/or orientation of the patient bones and tools in the coordinate system using the data from the tracking set 40. Moreover, once alterations are done, the tracking performed by the tracking controller 50 may be used to validate bone alterations, such as cut planes. In such a case, the surgical planning module 52 provides the planned alterations in the model of the bone.

Referring to FIGS. 1 and 2, the CAS controller 60 is shown in greater detail relative to the other components of the CAS system 10, including the EM tracking controller 50. The CAS controller 60 runs various modules, in the form of algorithms, code, non-transient executable instructions, etc, in order to operate the CAS system 10 in the manner described herein. In an embodiment, the CAS controller 60 may be part of any suitable processor unit, such as a personal computer or computers including laptops and desktops, tablets, server, etc. The CAS controller 60 may incorporate the EM tracking controller 50, or parts of it (e.g., some of the modules, such as the surgical tracking module 52). Moreover, the CAS controller 50 may share its processor unit with that of the EM tracking controller 50.

The CAS controller 60 may provide computer-assisted surgery guidance to an operator for instance in the form of surgical workflow and surgical data updated during the surgical procedure. Using the object tracking from the EM tracking controller 50, the CAS controller 60 may drive the robot arm 20 in performing the surgical procedure based on a surgery planning achieved pre-operatively. The CAS controller 60 may hence have a robot driver module 61. The robot driver module 61 is tasked with powering or controlling the various joints 22 of the robot arm 20 based on operator demands or on surgery planning. As shown with bi-directional arrows in FIG. 2, there may be some force feedback provided by the robot arm 20 to avoid damaging the bones, and to detect contact between the tool head 24, and anatomical features.

The robot driver module 61 may perform actions based on a surgery planning module 62. The surgery planning module 62 may be a module programmed specifically for any given patient, according to the parameters of surgery desired by an operator such as an engineer and/or surgeon. The parameters may include geometry of selected, planned bone cuts, planned cut depths, sequence or workflow of alterations with a sequence of surgical steps and tools, tools used, etc.

The surgical planning 62 may incorporate a navigation file to calibrate the robot arm 20 (e.g., through for robotized surgery), and/or the tools 30 with tracking sets 40, prior to commencing surgery. For example, the calibration subfile may include or use the virtual tool models B and virtual bone models C of the patient, for surface matching to be performed by the registration pointer 30', or such a registration pointer as used by the robot arm 20, for contacting the bone. The robot arm 20 would obtain a cloud of bone landmarks of the exposed bones, to reproduce a 3D surface of the bone. The 3D surface would then be matched to the bone model C of the patient, to set the 3D model in the X, Y, Z coordinate system, with the assistance of the surgical tracking module 52, in the manner described above. An operator's assistance may be requested initially, for instance to identify tracked landmarks. This may be part of the calibration subfile.

Referring to FIG. 2, the secondary tracking system 70 may optionally be used to supplement the tracking done by the tracking set 40 and EM tracking controller 50. For example, the secondary tracking system 70 may assist in providing additional accuracy in relating the position and orientation of the tool head 24 of the robot arm 20, or tools 30 and bones A to that of the tracking set 40, in the X, Y, Z coordinate system. According to an embodiment, the secondary tracking system 70 may comprise a camera that optically sees and recognizes retro-reflective markers optionally used to track the limbs in six DOFs, namely in position and orientation. A marker may be on the tool head 24 of the robot arm 20 such that its tracking allows the surgical tracking module 52 to calculate the position and/or orientation of the tool head 24 and tool 26A thereon. Markers may be fixed to the patient bones, such as the tibia and the femur. Markers attached to the patient need not be invasively anchored to the bone, as straps or like attachment means may provide sufficient grasping to prevent movement between the markers and the bones, in spite of being attached to soft tissue. However, the references could also be secured directly to the bones.

The markers can be provided in the form of retro-reflective markers or in the form of active emitters. As an alternative to optical tracking, the secondary tracking system 70 may consist of inertial sensors (e.g., accelerometers, gyroscopes, etc) that produce tracking data to be used by the surgical tracking module 52 to assist in continuously updating the position and/or orientation of the robot arm 20 and/or tools 30 and bones A (if equipped with an inertial sensor).

The secondary tracking system 70 may also be implemented by the sensors of the robot arm 20 (e.g., encoders) throughout the surgical procedure. The combination of the tracking set 40 and the sensors on the robot arm 20 may provide redundant tracking data ensuring that the surgical procedure meets the required precision and accuracy. In an embodiment featuring the robot arm 20, the surgical tracking module 52 may determine the position and orientation of the tool 24 from the robot driver module 61 using the encoders in the robot arm 20. In an embodiment, the position and orientation of the surgical tool 24 calculated by the tracking controller 50 with the EM sensors 41 may be redundant over the tracking data provided by the robot driver module 61 and robot arm sensors. However, the redundancy may assist in ensuring the accuracy of the tracking of the surgical tool. For example, the redundancy is used as a safeguard against incorrect tracking or distortion from the EM tracking controller 50, for instance due to bone movement or relative movement between the robot arm 20 and the patient and/or table. Also, the tracking of the tool 24 using the tracking set 40 and robot arm encoders may be used to detect any discrepancy between the primary and secondary tracking systems. For example, an improper mount of the tool 24 into the chuck of the robot arm 20 could be detected from the output of the tracking set 40, when verified against the position and orientation from the robot driver module 61. The operator may be prompted to verify the mount, via the interface 80. Alternatively or additionally, the secondary tracking system 70 can include another type of optical tracking technology such as the optical waveguide modeling technology, an embodiment of which is described further below.

The CAS system 10 may comprise various types of interfaces 80, for the information to be provided to the operator. The interfaces 80 may be monitors and/or screens including wireless portable devices (e.g., phones, tablets), audio guidance, LED displays, among many other possibilities. For example, the interface 80 comprises a graphic user interface (GUI) operated by the system 10. The interface 80 may also display images captured by cameras, for instance to be used in the collaborative/cooperative control mode of the system 10, or for visual supervision by the operator of the system 10, with augmented reality for example.

Figure 3:
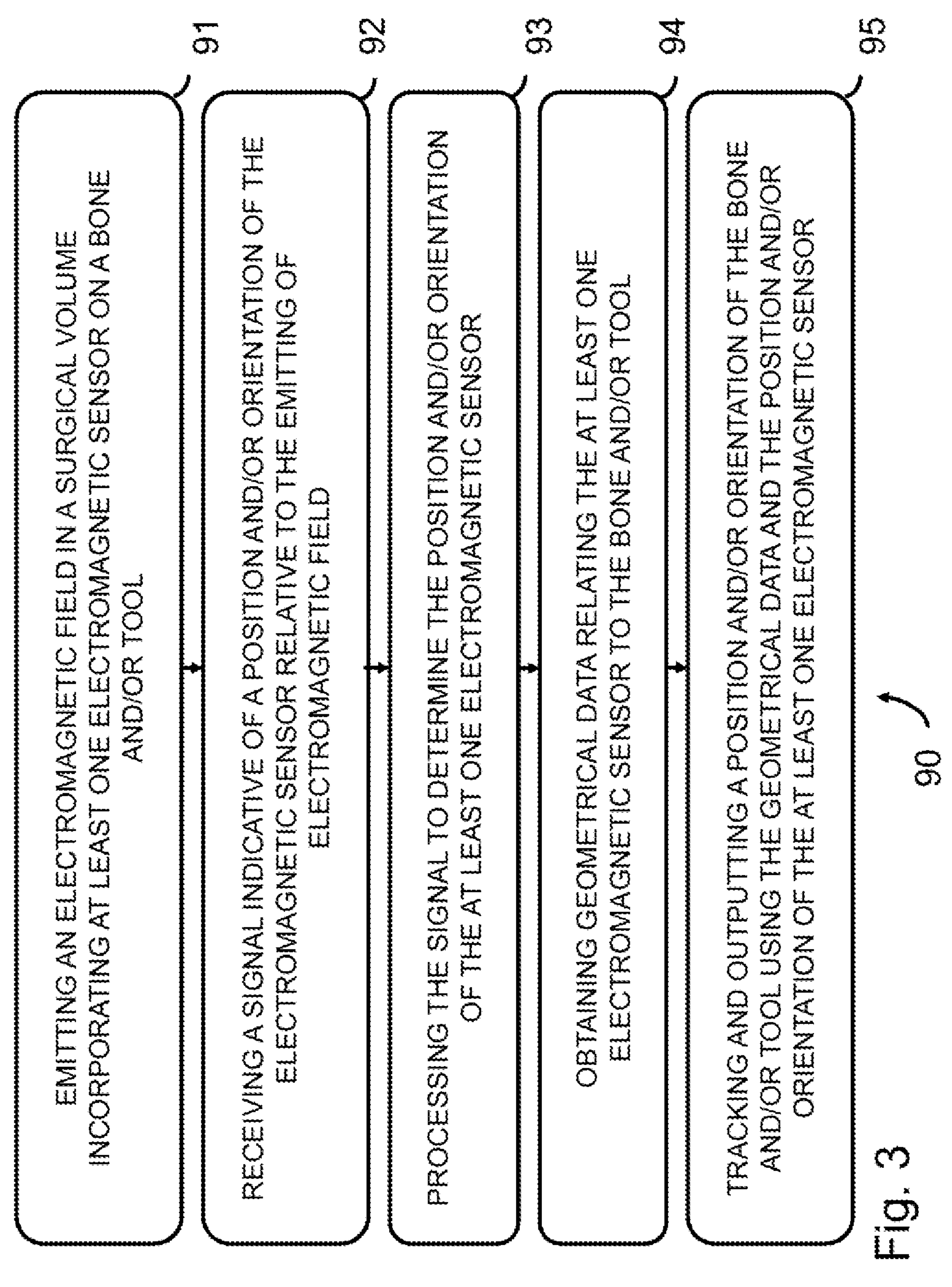
FIG. 3 is a flow chart of a method for tracking objects in robotized computer-assisted surgery, in accordance with one or more embodiments.

Referring to FIG. 3, a method for tracking one or more bones and objects such as tools, in computer-assisted surgery, using is generally shown at 90. The method 90 may be performed for instance by one or more processors related to the EM tracking controller 50 and/or CAS controller 60 (which may also be referred to as system), or by the CAS system 10 and its components as a whole as described above, as an example. Some or all of the steps of the method 90 may be inscribed on a non-transitory computer-readable memory communicatively coupled to the processing unit of the EM tracking controller 50 and/or CAS controller 60, for example in the form of computer-readable program instructions executable by the processing unit.

According to step 91, an electromagnetic field is emitted, using for instance the EM source 42, in a surgical volume incorporating one or more EM sensors 41 on a bone A and/or tool 30. According to an embodiment, 91 includes operating or driving the EM source 42 to emit the electromagnetic field. The step 91 of emitting may be continuous.

According to step 92, a signal indicative of a position and/or orientation of the EM sensor(s) 41 relative to the emitting of electromagnetic field is received. According to an embodiment, step 92 includes operating or driving the EM sensor to receive the signals. The step 92 of receiving may be continuous.

According to step 93, the signal received by the EM sensor(s)s is processed, to determine the position and/or orientation of the EM sensor(s) 41. In an embodiment, the position and/or orientation may be in an X,Y,Z referential system and may include 6 DOFs for the EM sensor(s) 41.

According to step 94, geometrical data relating the EM sensor(s) 41 to its associated bone A and/or tool 30 is obtained. This may include receiving an identity of the bone A and/or tool 30 associated to the EM sensor(s) 41. The geometrical data of step 94 may include accessing or generating models or surfaces of the objects to be tracked, such as tool models B and bone models C. The generating of surfaces may be that of a three-dimensional geometry of a surface of the bone, the three-dimensional geometry of the surface being in the coordinate system. According to step 94, the models may be merged to the position and/or orientation of the EM sensor(s) 41, and to generated surfaces. In step 94, the merge may optionally be validated, for instance using a calibration device. Step 94 may also include determining a spatial relationship between an object being tracked and the preoperative 3D model of the object. Stated differently, step 94 may include determining a position and orientation of the bone or other object in the coordinate system by matching the three-dimensional geometry of the surface of the at least one bone to a three-dimensional model of the bone.

In step 95, a position and/or orientation of the bone A and/or tool(s) 30 is continuously tracked and output, using the geometrical data and the position and/or orientation of the EM sensor(s) 41. The output may be in the form of angles, position and/or orientation data, images, etc. The continuous output may include imaging of bone alterations, such as cut planes, for such bone alterations to be validated in comparison to surgical planning.

According to step 95, the position and orientation of the bone(s) in the coordinate system is continuously output to the robot driver 51 controlling the robot arm 20 supporting the surgical tool 24 in the coordinate system for altering the bone. The position and orientation of the bone(s) in the coordinate system may be continuously output with the position and orientation of the surgical tool in the coordinate system.

Figures 4, 4A:
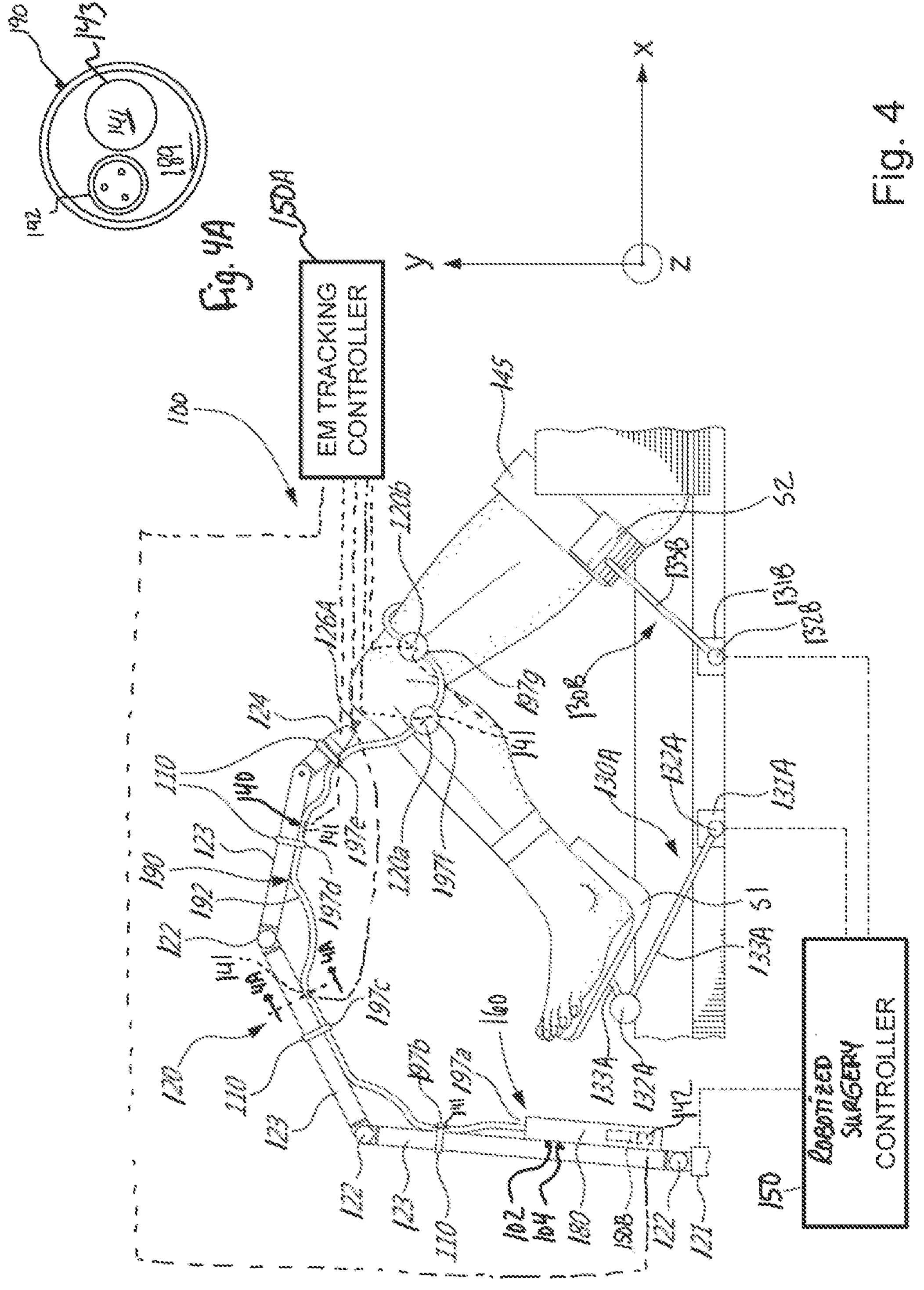
FIG. 4 is a schematic view of an example of a CAS system incorporating an example dual tracking system with an electromagnetic tracking set and an optical waveguide modeling system, in accordance with one or more embodiments.
FIG. 4A is a sectional view of a dual tracking cable of the dual tracking system of FIG. 4, taken along section 4A-4A of FIG. 4, in accordance with one or more embodiments.

The secondary tracking system can be provided in different forms. For instance, FIG. 4 illustrates an example of a CAS system 100 having a primary tracking system 102 incorporating an electromagnetic tracking set 140 such as the one described above, and a secondary tracking system 104 provided in the form of an optical waveguide modeling (OWM) system 160. As such, the CAS system 100 uses two independently different yet complementary tracking technologies for redundancy purposes in some embodiments. As depicted, some components of the electromagnetic tracking set 140 of the primary tracking system 102, e.g., at least some EM sensors 141, are distributed along a dual tracking cable 190. The secondary tracking system 104 has a multi-core optical fiber 192 which also extends along the dual tracking cable 190 in this specific embodiment. Accordingly, the position and/or orientation of the dual tracking cable 190 may be determined by both the primary and secondary tracking systems 102 and 104, in an independent and complementary manner.

The CAS system 100 is used to perform orthopedic surgery maneuvers on a patient, including pre-operative analysis of range of motion and implant assessment planning, as described hereinafter. The CAS system 100 is shown relative to a patient's knee joint in supine decubitus, but only as an example. The CAS system 100 could be used for other body parts, including non-exhaustively hip joint, spine, and shoulder bones. A particular function of the CAS system 100 is assistance in planning soft tissue balancing, whereby the CAS system 100 may be used in total knee replacement surgery, to balance tension/stress in knee joint ligaments.

In addition to the primary tracking system 102 and the secondary tracking system 104, the CAS system 100 has a robot arm 120, a foot support 130A, a thigh support 130B, a robotized surgery controller 150, a primary tracking system 102 and a secondary tracking system 104:

The robot arm 120 is the working end of the CAS system 100, and is used to perform bone alterations as planned by an operator and/or the robotized surgery controller 150 and as controlled by the robotized surgery controller 150;

The foot support 130A supports the foot and lower leg of the patient, in such a way that it is only selectively movable. The foot support 130A is robotized in that its movements can be controlled by the robotized surgery controller 150;

The thigh support 130B supports the thigh and upper leg of the patient, again in such a way that it is only selectively or optionally movable. The thigh support 130B may optionally be robotized in that its movements can be controlled by the robotized surgery controller 150;

The robotized surgery controller 150 controls the robot arm 120, the foot support 130A, and/or the thigh support 130B. Moreover, as described hereinafter, the robotized surgery controller 150 may perform a range-of-motion (ROM) analysis and implant assessment in pre-operative planning, with or without the assistance of an operator;

The primary tracking system 102 has the EM tracking set 140 which includes one or more EM sensors 141 and one or more EM source(s) 142, that are collectively used for electromagnetic tracking;

The EM tracking controller 150A operates the EM tracking set 140, and is tasked with determining the position and/or orientation of the various relevant objects during the surgery procedure, such as the bone(s), organ(s) and tool(s), using data acquired by the EM tracking set 140 for navigation in a coordinate system such as the X, Y, Z coordinate system (also known as frame of reference, global reference system, etc). The EM tracking set 140 may also be used in non-robotized surgery as well;

The secondary tracking system 104 has the OWM system 160 which is also used to track the robot arm 120 and the patient limb(s) or bone(s) in this embodiment. More specifically, the OWM system 160 assists in performing the calibration of the patient bone with respect to the robot arm 120, for subsequent navigation in the X, Y, Z coordinate system. The OWM system 160 may also be used in non-robotized surgery as well;

The OWM controller 150B operates the OWM system 160, and is tasked with determining the position and/or orientation of the various relevant objects during the surgery procedure, such as the bone(s), organ(s) and tool(s), using date acquired by the OWM system 160 for navigation in a coordinate system, e.g., the X, Y, Z coordinate system. The OWM system 160 may also be used in non-robotized surgery as well; and It is noted that although the robotized surgery controller 150, the EM tracking controller 150A and the OWM controller 150B are shown as separate components, the robotized surgery controller 150, the EM tracking controller 150A and the OWM controller 150B can be provided in the form of a single controller in some embodiments.

Still referring to FIG. 4, a schematic example of the robot arm 120 is provided. The robot arm 120 may stand from a base 121, for instance in a fixed relation relative to the operating-room or table supporting the patient in some specific embodiments. Indeed, the relative positioning of the robot arm 120 relative to the patient is a determinative factor in the precision of the surgical procedure, whereby the foot support 130A and thigh support 130B may assist in keeping the operated limb fixed in the illustrated X, Y, Z coordinate system. However, it will be appreciated that the fixed relation between the base 121 and operating-room or table is only optional, as will be described below. The robot arm 120 has a plurality of joints 122 and links 123, of any appropriate form, to support a tool head 124 that interfaces with the patient. The arm 120 is shown being a serial mechanism, arranged for the tool head 124 to be displaceable in sufficient degrees of freedom (DOF). For example, the robot arm 120 controls 6-DOF movements of the tool head 124, i.e., X, Y, Z in the coordinate system, and pitch, roll and yaw. Fewer or additional DOFs may be present. For simplicity, only a generic illustration of the joints 122 and links 123 is provided, but more joints of different types may be present to move the tool head 124 in the manner described above. The joints 122 are powered for the robot arm 120 to move as controlled by the robotized surgery controller 150 in the six DOFs. Therefore, the powering of the joints 122 is such that the tool head 124 of the robot arm 120 may execute precise movements, such as moving along a single direction in one translation DOF, or being restricted to moving along a plane, among possibilities.

The tool head 124 supports a burr 126A, used to resurface a bone. As a non-exhaustive example, other tools that may be supported by the tool head 124 include a registration pointer, a reamer, a reciprocating saw, a retractor, a cut guide and the like, depending on the nature of the surgery. The various tools may be part of a multi-mandible configuration or interchangeable, whether with human assistance, or as an automated process. The installation of a tool in the tool head 124 may then require some calibration in order to track the installed tool in the X, Y, Z coordinate system of the robot arm 120.

In order to preserve the fixed relation between the leg and the coordinate system, and to perform controlled movements of the leg as described hereinafter, a generic embodiment is shown in FIG. 4. The foot support 130A may be displaceable relative to the OR table, in order to move the leg in flexion/extension (e.g., to a fully extended position and to a flexed knee position), with some controlled lateral movements being added to the flexion/extension. Accordingly, the foot support 130A is shown as having a robotized mechanism by which it is connected to the OR table, with sufficient DOFs to replicate the flexion/extension of the lower leg. Alternatively, the foot support 130A could be supported by a passive mechanism, with the robot arm 120 connecting to the foot support 130A to actuate its displacements in a controlled manner in the coordinate system. The mechanism of the foot support 130A may have a slider 131A, moving along the OR table in the X-axis direction. Joints 132A and links 133A may also be part of the mechanism of the foot support 130A, to support a foot interface S1 receiving the patient's foot.

The tight support 130B may be robotized, static or adjustable passively. In the latter case, the thigh support 130B may be displaceable relative to the OR table, in order to be better positioned as a function of the patient's location on the table. Accordingly, the thigh support 130B is shown as including a passive mechanism, with various lockable joints to lock the thigh support 130B in a desired position and orientation. The mechanism of the thigh support 130B may have a slider 131B, moving along the OR table in the X-axis direction. Joints 132B and links 133B may also be part of the mechanism of the thigh support 130B, to support a thigh bracket S2. A strap 145 can immobilize the thigh/femur in the thigh support 130B. The tight support 130B may not be necessary in some instances. However, in the embodiment in which the range of motion is analyzed, the fixation of the femur via the thigh support 130B may assist in isolating joint movements.

As depicted, the EM tracking set 140 includes one or more EM sensor(s) 141 and one or more EM source(s) 142, that are used for primary, electromagnetic tracking. In some embodiments, the EM tracking set 140 uses tuned AC electromagnetic technology for the tracking of the EM sensors 141 in position and orientation relative to a referential space, such as the X, Y, Z coordinate system.

In the illustrated embodiment, a series of EM sensors 141 are distributed along a dual tracking cable 190. As depicted, a portion of the dual tracking cable 190 may be mounted to the robot arm 120 so as to determine a position and/or orientation of the robot arm 120. The dual tracking cable 190 may have another portion mounted to bone(s) and/or organ(s) of the patient or surgery tools to determine a position and/or orientation of the bone(s) and/or organ(s). Calibration steps and/or interactions with the EM tracking controller 150A may be required in transitioning one of the EM sensors 141 from one portion of the dual tracking cable 190 to another.

Each EM sensor 141 has coil(s) to detect a magnetic flux resulting from a electromagnetic field produced by the EM source(s) 142. In an embodiment, one or more of the EM sensors 141 has three non-parallel sensor coils that, when paired with a given EM source 142, may produce position and/or orientation tracking in a referential system including the EM source 142. The tracking may be for both position and orientation, i.e., six degrees of freedom, X, Y, Z in a coordinate system, and pitch, roll and yaw. Fewer or additional DOFs may be tracked. The EM sensors 141 may include different types of sensor components, such as solid-state sensors, quantum, or flux gage sensors. In an embodiment, the solid-state sensors implement giant magnetoresistance (GMR). The sensors 141 may also include superconducting quantum interference device (SQUID) magnetometers and the like. As shown in this example, the EM source 142 is enclosed in a housing mounted to a portion of the robot arm 120. More specifically, and as described below, the housing in which the EM source 142 is housed may also house one or more components of the OWM system 160 such as the optical device 180.

The EM sensors 141 may be applied directly against the objects (e.g., robot arm 120, tools 126A and/or bones), or indirectly via the dual tracking cable 190. The EM sensors 141 employing the afore-mentioned technologies may be relatively small in size, e.g., in the range of millimeters, and can be secured non-invasively to bones, and soft tissue. Any appropriate type of securing means may be used, including staples, adhesives, among others. The positioning of such small-size EM sensors 141 on bones, robot arm portions, and tools may be random, provided the EM sensors 141 are fixed to the object.

In another embodiment, the EM sensors 141 have their electronic components (e.g., coils and/or circuitry) embedded in a casing and/or cable. The EM sensors 141 may optionally be calibrated, in that a geometry of the casing and/or cable may be known along with location of the sensor components inside the casing and/or cable. Therefore, as described below, a calibration of the CAS system 100 may be facilitated by the use of a calibrated casing or cable for the EM sensors 141, even though optional. As best shown in the sectional view of FIG. 4A, the EM sensors 141 are distributed along an EM sensor cable 143 which runs alongside a multicore optical fiber 192 of the OWM system 160 within the dual tracking cable 190. The dual tracking cable 190 can have a sheath-like body enclosing the EM sensor cable 143 along with the multicore optical fiber 192. Insulation material 189 may snugly receive the EM sensor cable 143 and the multicore optical fiber 192 within the dual tracking cable 190. In some embodiments, the EM sensor cable 143 and the multicore optical fiber 192 are used to independently monitor a position and/or orientation of the robot arm 120, the bone(s) and/or the organ(s) of the patient in a simultaneous manner. The EM sensor cable 143 and the multicore optical fiber 192 need not to be part of a single cable. However, in some embodiments, it was found preferable to make the EM sensor cable 143 and the multicore optical fiber 192 integral to a single, dual tracking cable to minimize any spatial discrepancies that could occur with two different tracking cables. Manipulations are also reduced and facilitated by using a single cable such as dual tracking cable 190.

In this embodiment, the EM source 142 is an EM transmitter, emitting an electromagnetic field, such as an electromagnetic dipole field. In an embodiment, the EM source 142 produces a modulated AC electromagnetic field (modulated waveform), with the AC electromagnetic field having induction-vector components that will be detected and measured using the EM sensors 141. The EM source 142 may have source coils to produce the electromagnetic field. In an embodiment, there are three source coils in the EM source 142, arranged in a non-parallel manner, for the 6-DOF tracking, and electronic circuitry to control the generation of the electromagnetic field. For instance, the electronic circuitry may control the magnitude and phase of the modulated electromagnetic field. Further, the EM source 142 may produce an electromagnetic field with a modulation frequency that is close to the frequency of the EM sensors 141. The EM source 142 may for instance emit a single-tone signal, with amplitude or frequency modulation.

The EM source 142 may be positioned in a fixed manner in relatively close proximity to the surgical volume, so as to be close to the EM sensors 141, and hence avoid interference from larger metallic objects. Consequently, the location of the EM source 142 can be fixed in the referential system, and may therefore designate the origin of the referential system. In an embodiment, the origin may be arbitrarily positioned. In some embodiments, more than one EM source 142 are configured to emit respective electromagnetic fields of different frequencies. In these embodiments, the EM sensors may be configured to sense the electromagnetic fields of different frequencies. In some embodiments, a first set of EM sensors 141 are configured to sense the electromagnetic field of a first frequency whereas a second set of EM sensors 141 are configured to sense the electromagnetic of a second frequency different from the first frequency, and so forth for different frequencies. Such redundancy may be useful for confirming the tracking of tool(s) or bone(s) in quasi real time. It is noted that as the signals propagating along the multicore optical fiber 192 are guided, there can be no or quasi no crosstalk with the electromagnetic field emitted by the EM source 142.

Still referring to FIG. 4, the EM tracking controller 150A may be part of any suitable processor unit, such as a personal computer or computers including laptops and desktops, tablets, server, etc. The EM tracking controller 150A runs various modules, in the form of algorithms, code, non-transient executable instructions, etc, in order to track the robot arm 120, tools and/or bones or organs in the manner described herein. The EM tracking controller 150A may be a subpart of the robotized surgery controller 150, or an independent unit. The tracking controller 150A operates the tracking set 140, so as to receive and process signals from the EM tracking set 40 to compute position and/or orientation data, i.e., to determine the relative position of the objects.

The tracking performed by the primary tracking system 102 can be validated using the secondary tracking 104. As depicted, the secondary tracking 104 incorporates the OWM system 160 such as the one described in U.S. Pat. No. 10,292,774, the content of which is incorporated herein by reference. As shown, the OWM system 160 has an optical device 180, a multicore optical waveguide optically coupled to the optical device 180 and a OWM controller 150B communicatively coupled to the optical device 180. The OWM controller 150B is shown as part of the optical device 180, but could also be standalone, or part of the robotized surgery controller 150. As shown in this example, the multicore optical waveguide is provided in the form of a multicore optical fiber 192. In some other embodiments, however, the multicore optical waveguide may be provided in the form of a multicore strip waveguide and the like.

Figure 5:
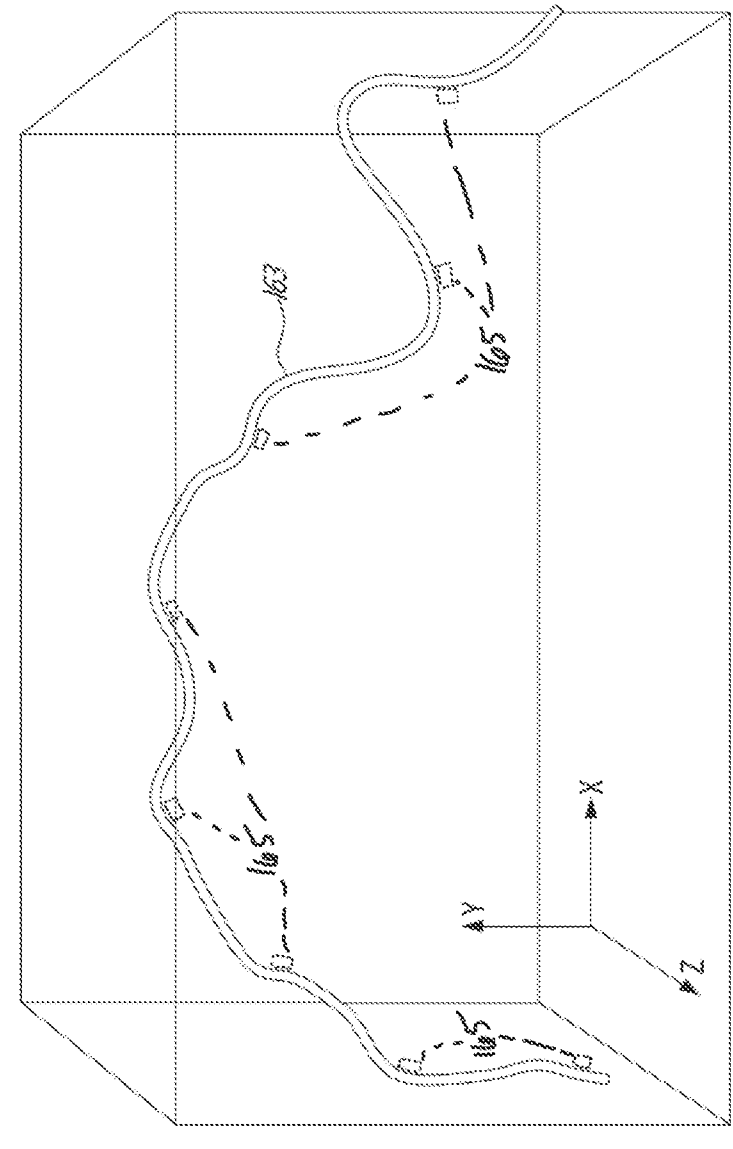
FIG. 5 is a graph representing an example waveguide model of a multicore optical fiber of the optical waveguide modeling system and of exemplary electromagnetic sensor models of the electromagnetic tracking set of FIG. 4, in accordance with one or more embodiments.

In this embodiment, the optical device 180 is configured for transmitting optical signals along the multicore optical fiber 192 and for receiving return optical signals from the multicore optical fiber 192. Further, the optical device 180 is configured to transmit electric signals to the OWM controller 150B, the electric signals being representative of the received return optical signals. Based on the received electric signals, the OWM controller 150B is adapted and configured to generate a three-dimensional waveguide model representing the shape and orientation of the multicore optical fiber 192 at a specific moment in time. For instance, FIG. 5 shows a plot of a waveguide model 163 generated by the OWM controller 150B, which represents the position and orientation of the multicore optical fiber 192 shown in FIG. 4. As shown in this example, EM sensor models 165 representing the position and/or orientation of the EM sensors 141 are also shown. In some embodiments, the EM sensor models 165 are determined by the EM tracking controller 150A whereas the waveguide model 163 is determined by the OWM controller 150B. Preferably, the EM sensor models 165 and the waveguide model 163 are registered to a same reference coordinate system X, Y, Z so as to appreciate the correspondence, or lack of correspondence, between the models 163 and 165.

In some embodiments, the position and/or orientation of the waveguide model 163 and the position and/or orientation of the EM sensor models 165 are continuously compared to one another, and when a discrepancy exceeding a given threshold is detected, an alert is generated. The alert can be indicated to the surgical environment via for example a visual, auditory or haptic indicator(s) in some embodiments. The alert may be stored on a memory system, or communicated to an external network, in some other embodiments.

Accordingly, by monitoring the waveguide model over time, the OWM system 160 allows the monitoring of the shape and the orientation of the multicore optical fiber 192 in real time or quasi real time. In some embodiments, the OWM system 160 generally has a small footprint and is lightweight, which can provide the ability to track instruments such as the tool head 124, bones and limbs, with a millimeter-level accuracy.

As depicted, the OWM system 160 has one multicore optical fiber 192, having for example a diameter of 200 microns and has an axial length up to a few meters. However, in some other embodiments, the OWM system 160 can have more than one multicore optical fiber, with different diameters and/or different axial lengths.

Figure 6:
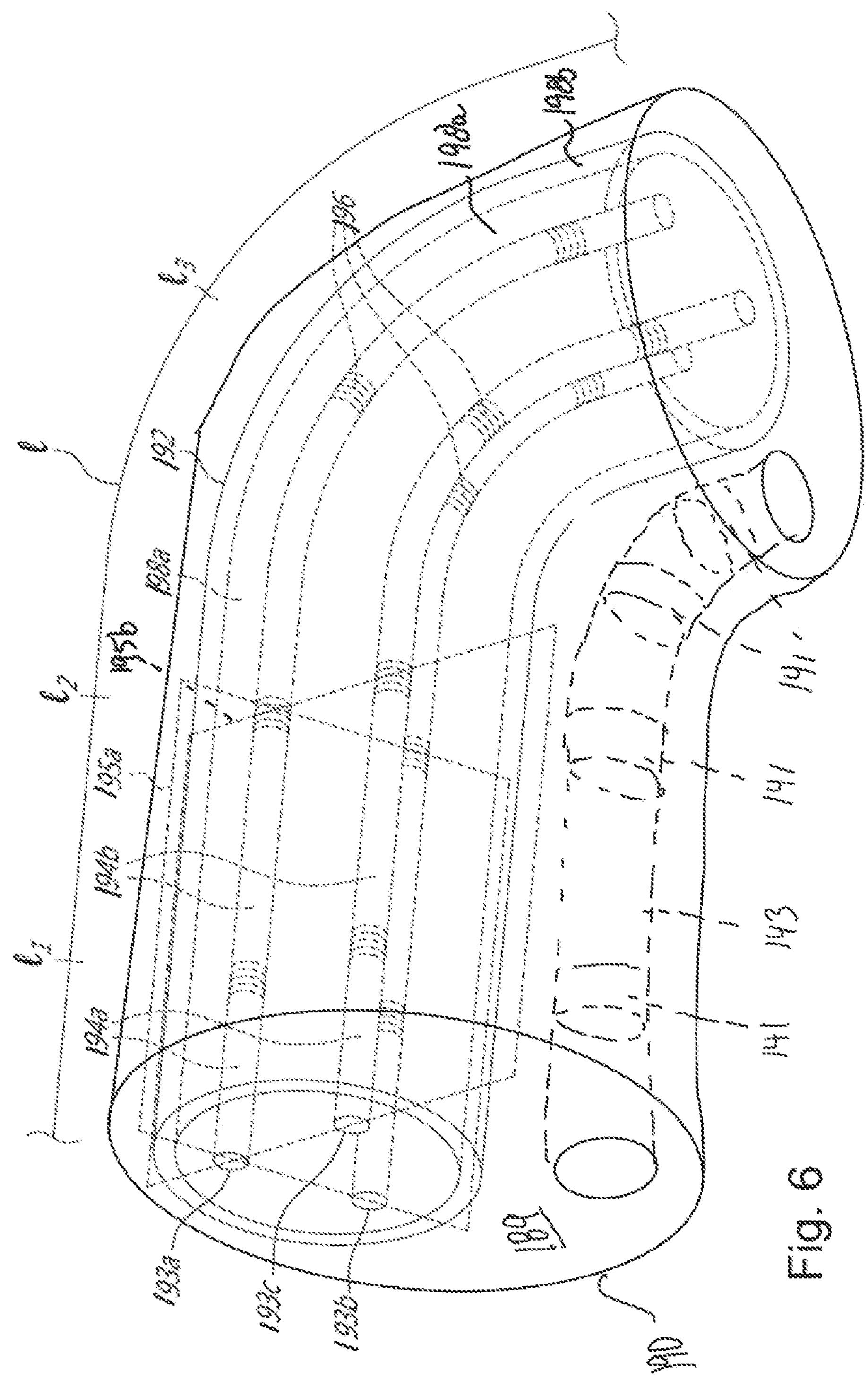
FIG. 6 is an enlarged view of a portion of the dual tracking cable of FIG. 4, showing fiber Bragg grating triplets and electromagnetic sensors distributed longitudinally along the dual tracking cable, in accordance with one or more embodiments.

FIG. 6 shows a portion of the dual tracking cable 190 shown in FIGS. 4 and 4A. More specifically, there is shown a portion of the EM sensor cable 143 along with a corresponding portion of the multicore optical fiber 192.

As illustrated, the EM sensor cable 143 has a series of longitudinally distributed EM sensors 141. The EM sensors 141 may sense the electromagnetic field emitted by the EM source 142 independently from one another, thereby allowing the determination of the position and/or orientation of each one of the EM sensors 141 by the EM tracking controller 150A. Although the EM sensors 141 are shown as part of a EM sensor cable in this embodiment, it is intended that the EM sensors 141 can be independent from each other. Moreover, in some embodiments, the EM sensors 141 are mounted on an exterior surface of the multicore waveguide fiber 192 instead of being part of the larger sheath-like dual tracking cable 190.

As depicted, the multicore optical fiber 192 has three cores 193*a*, 193*b*, 193*c* which extend along an axial length l of the multicore optical fiber 192. In some other embodiments, the multicore optical fiber 192 can have more than three cores. For instance, the multicore optical fiber 192 can have four cores.

In this example, the cores 193*a*, 193*b* and 193*c* are embedded in an inner cladding 198*a*. The inner cladding 198*a* generally has a refractive index which is lower than a refractive index of each one of the cores 193*a*, 193*b* and 193*c*. The refractive index of the cores 193*a*, 193*b* and 193*c* need not to be identical from one core to another. The multicore optical fiber 192 has an outer cladding 198*b* surrounding the inner cladding 198*a*. Moreover, the multicore optical fiber 192 can be provided with a sheath covering the outer cladding 198*b*, for at least some providing mechanical resistance to the multicore optical waveguide 192.

As depicted, the cores 193*a*, 193*b* and 193*c* are off-axis and circumferentially spaced-apart from one another. In this example, the cores 193*a*, 193*b* and 193*c* are circumferentially spaced-apart by 60°. It is contemplated that the cores 193*a*, 193*b* and 193*c* are sufficiently spaced-apart from one another to prevent cross-talk between the cores 193*a*, 193*b* and 193*c*. In this specific example, each core 193*a*, 193*b*, 193*c* is sized and shaped to be single-mode for light having a wavelength of 1550 nm. In alternate embodiments, however, each core may be sized and shaped to be multimode.

The OWM system 160 involves distributed strain measurements in each of the cores 193*a*, 193*b* and 193*c* of the multicore optical fiber 192, at different axial positions Ii along its axial length l, to construct the waveguide model 163. In this example, i is an integer ranging from 1 and a number N of axial positions. The axial increment ΔI between two successive axial positions Ii can be in the order of the millimeter for example. The axial increments ΔI between successive axial positions Ii need not be identical for each pair of successive axial positions Ii where strain measurements are taken. In some embodiments, the EM sensors 141 may be also spatially spaced-apart from one another by axial increment ΔI. However, in some other embodiments, the EM sensors 141 may be axially spaced-apart by an axial increment greater than the axial increments ΔI.

To measure strain in a unicore waveguide, light is sent down the core of the waveguide, where wavelengths of the reflected light are a function of the strain on the core and its temperature. To reduce the effect of temperature, the sheath of the multicore optical fiber can provide thermal insulation. In the context of the multicore optical fiber 192, however, bending of the multicore optical fiber 192 induces strain on each one of the cores 193*a*, 193*b* and 193*c*, which can be measured by monitoring the reflected wavelengths from each core 193*a*, 193*b*, 193*c*. The induced strains are a function of the local degree of bending of the multicore waveguide fiber 192. For instance, more strain is induced in the multicore optical fiber 192 around its elbow portion than in any of its straight portions.

The cores 193*a*, 193*b* and 193*c* allow at least two non-coplanar pairs of cores to be formed. For instance, in this embodiment, the cores 193*a* and 193*b* form a first pair 194*a* of cores lying in a first plane 195*a*, and the cores 193*a* and 193*c* form a second pair 194*b* of cores lying in a second plane 195*b* that is not coplanar with the first plane 195*a*. As having only the first pair 194*a* of cores would allow reconstruction of the bending of the corresponding waveguide only in the first plane 195*a*, having the two non-coplanar pairs 194*a* and 194*b* of cores can allow reconstruction of the bending of the corresponding waveguide in both the first and second planes 195*a* and 195*b*, thus allowing a three dimensional model of the multicore optical fiber 192 to be determined.

For instance, a first strain measurement at a first axial position 11 in the first core 193*a* can be compared to a second strain measurement at the first axial position 11 in the core 193*b* to determine a relative strain in the first plane 195*a* comprising the first pair 194*a* of cores. Similarly, the first strain measurement can be compared to a third strain measurement at the first axial position 11 in the core 193*c* to determine a relative strain in the second plane 195*b* comprising the second pair 194*b* of cores.

By doing so, the OWM controller 150B combines the relative strains in the first and second planes 195*a* and 195*b* and arrive with a strain distribution in the multicore optical fiber 192 at the first axial position 11. Then, a strain distribution of the multicore optical fiber 192 at a second axial position 12 along the multicore optical fiber 192 is determined. By comparing the strain distributions at the first and second axial positions 11 and 12, the shape and orientation of the multicore optical fiber 192 between the first and second axial positions 11 and 12 can be determined by the processor unit 150B. The strain distribution is then determined at a third axial position 13 along the multicore optical fiber 192, which can be used to determine the shape and orientation of the multicore optical fiber 192 between the second and third axial positions 12 and 13, and so forth, until the shape and orientation of the whole multicore optical fiber 192 is determined.

In this embodiment, such distributed strain measurements are based on fiber Bragg gratings (FBGs) 196. Broadly described, each FBG 196 comprises a series of modulations of the refractive index of the corresponding core to generate a spatial periodicity in the refraction index. The spacing of the modulations is chosen so that each index change causes reflection of a narrow band of wavelengths, and lets other wavelengths pass through. During fabrication of the FBG, the modulations are spaced by a known distance, thereby causing reflection of a known band of wavelengths, which is generally referred to as the Bragg wavelength. However, when a strain is induced on any one of the cores 193*a*, 193*b* and 193*c*, the spacing of the modulations can change depending on the amount of strain in the corresponding core, and so does the Bragg wavelength of the corresponding FBG 196.

Accordingly, in this embodiment, each core 193*a*, 193*b*, 193*c* of the multicore optical fiber 192 has an array of FBGs 196 inscribed at different axial positions Ii along their respective axial lengths. If located at axial positions Ii where the multicore optical fiber 192 is bent, the FBGs 196 can thereby be used to determine the amount of bending at those axial positions Ii. The strain measurements, combined with the known spacing distances between each FBG 196, can be used to reconstruct the waveguide model 163. It is noted that although the illustrated embodiment shows a number of triplets of FBGs 196 corresponding to a number of EM sensors 141, it is expected that the number of FBG triplets can differ from the number of EM sensors 141. In some embodiments, the number of FBG triplets is greater than the number of EM sensors 141.

Such distributed strain measurements can also be based on inherent backscattering in any one of the cores 193*a*, 193*b* and 193*c*, also known as Rayleigh backscattering. In this embodiment, the optical signals received from the cores of the multicore optical fiber includes Rayleigh scattering or any other suitable type of backscattering. Rayleigh scatter occurs as a result of defects distributed along the cores of the multicore optical fiber causing random fluctuations of the refractive index in each of the cores of the multicore optical fiber. These random fluctuations can result in localized reflective interfaces which can reflect more or less some wavelengths along the cores of the multicore optical fiber. By monitoring such backscattering from each core of the multicore optical fiber, distributed strain measurements can also be performed. For various reasons, including consistency, predictability and reflectivity, fiber Bragg gratings 196 are generally preferred over such Rayleigh backscattering techniques.

Many ways of interrogating the FBGs 196 and distinguishing the readings from each FBG 196 exist and can be used by the OWM controller 150B. In some embodiments, optical frequency domain reflectometry (OFDR) can be used in which the FBGs 196, with the same grating period, are placed along each of the cores 193*a*, 193*b* and 193*c*. Each core 193*a*, 193*b*, 193*c* can be terminated with a partially reflecting mirror (not shown). The FBGs 196 are placed in such a way that the distance from each FBG 196 to the partially reflecting reflector is known, which causes the reflection spectrum of each FBG 196 to be modulated with a distinct modulation frequency, thereby allowing the individual reflection spectra to be determined. In addition, OFDR may be used to interrogate the array of FBGs 196 with sufficiently low delays such that that the bending data can be used as a feedback signal in a real-time motion control loop.

Sensors for determining a shape and orientation of a multicore optical fiber 192 have been used. For example, optical fibers including FBGs have been used in a variety of applications for providing strain measurements in multicore optical fibers. Examples of such systems are described in U.S. patent application publication no. 2006/0013523, filed on Jul. 13, 2005, U.S. provisional patent application Ser. No. 60/588,33A6, filed on Jul. 16, 2004, and U.S. Pat. No. 6,389,187, filed on Jun. 17, 1998. Examples of commercially available sensors for determining a shape and orientation of an optical fiber can be purchased from a variety of sources, such as Smart Fibres Ltd. of Bracknell, England, or Luna Innovations. Inc. of Blacksburg, Va.

Still referring to FIG. 6, the multicore optical fiber 192 has an ending portion 197*a* which is optically coupled to the optical device 180 and by which optical signals are transmitted and received.

The optical device 180, via the OWM controller 150B, is used to measure the distributed strain measurements from the multicore optical fiber 192. More specifically, the optical device 180 can include one or more optical sources, one or more optical detectors, electrical connections, optical waveguides such as fibers, optical couplers and the like so as to send optical signal in the cores 193*a*, 193*b* and 193*c* of the multicore optical fiber 192 and receive optical signals therefrom, from which the distributed strain measurements can be determined.

Robot arm attachments 110 can be used to attach different portions of the multicore optical fiber 192 to the links 123 and to the tool head 124 of the robot arm 120. More specifically, portions 197*b*, 197*c* and 197*d* of the multicore optical fiber 192 are attached to corresponding links 123 and portion 197*e* of the multicore optical fiber 192 is attached to the tool head 124. In an embodiment, the joints 122 of the robot arm 120 have position encoders or sensors such that the robotized surgery controller 150 may track the position of each point along the robot arm without attaching the multicore optical fiber 192 to the links 123. In such an embodiment, the multicore optical fiber 192 need only be attached to the robot arm 120 at the tool head 124 in order to implement tracking of the lower leg and thigh of the patient in the X, Y, Z coordinate system, as described herein. An example of such a robot arm is the TX60 industrial robot of Staubli Robotics of Faverges, France.

Limb attachments 120*a* and 120*b* are used to attach different portions of the multicore optical fiber 192 to a respective one of the lower leg (e.g., tibia) and the thigh (e.g., femur) of the patient. More specifically, portion 197*f* of the multicore optical fiber 192 is attached to the lower leg of the patient and portion 197*g* of the multicore optical fiber 192 is attached to the thigh of the patient.

The limb attachments 120*a* and 120*b* attached to the patient need not be invasively anchored to the bone, as straps or like attachment means can provide sufficient grasping to prevent movement between the limb attachments 120*a* and 120*b*, the corresponding portion of the multicore optical fiber 192 and the bones, in spite of being attached to soft tissue. However, in some other embodiments, the limb attachments 120*a* and 120*b* are provided in the form of bone attachments which are invasively anchored to the bones.

The present disclosure refers to the CAS system 10 as performing continuous tracking. This means that the tracking may be performed continuously during discrete time periods of a surgical procedure, in real time. Continuous tracking may entail pauses, for example when the bone is not being altered. However, when tracking is required, the system 10 may provide a continuous tracking output, with any disruption in the tracking output triggering an alarm or message to an operator.

The invention claimed is:

1. A system for tracking at least one tool relative to a bone in computer-assisted surgery, comprising:
- a processing unit; and
- a non-transitory computer-readable memory communicatively coupled to the processing unit and comprising computer-readable program instructions executable by the processing unit for:
  - calibrating a surface of a bone and/or tool relative to at least one electromagnetic sensor by registering a geometrical relation of points of the surface of the bone and/or tool relative to the at least one electromagnetic sensor;
  - continuously emitting an electromagnetic field in a surgical volume incorporating the at least one electromagnetic sensor on the bone and/or tool;
  - continuously receiving a signal indicative of a position and/or orientation of the at least one electromagnetic sensor relative to the emitting of electromagnetic field;

processing the signal to determine the position and/or orientation of the at least one electromagnetic sensor; and continuously tracking and outputting a first position and/or orientation of the bone and/or tool using the geometrical data and the position and/or orientation of the at least one electromagnetic sensor.

2. The system of claim 1 wherein continuously emitting includes continuously emitting electromagnetic fields of different frequencies.

3. The system of claim 1 wherein the outputting includes imaging the bone and/or tool.

4. The system of claim 1 further comprising moving a robot arm based on the outputting of the first position and/or orientation of the bone and/or tool.

5. The system of claim 1 further comprising, using an optical waveguide modeling system having at least one multicore optical fiber with at least one portion attached to the bone and/or tool, generating a waveguide model representing the multicore optical fiber as attached to the bone and/or tool; and continuously tracking and outputting a second position and/or orientation of the bone and/or tool using the waveguide model.

6. The system of claim 5 further comprising comparing the first position and/or orientation of the bone and/or tool to the second position and/or orientation of the bone and/or tool.

7. The system of claim 5 further comprising generating an alert upon determining a difference exceeding a threshold between the first and second positions and/or orientations of the bone and/or tool.

8. The system of claim 1, further comprising:

at least one electromagnetic source;

at least one electromagnetic sensor configured to be secured to a bone and/or a tool; and a computer-assisted surgery controller for continuously driving the electromagnetic source to emit the electromagnetic field in the surgical volume incorporating the at least one electromagnetic sensor.

9. The system of claim 8 further comprising continuously displaying the first position and/or orientation of the bone and/or tool on a display screen.

10. The system of claim 8 further comprising a robot arm moved based on the first position and/or orientation of the bone and/or tool.

11. The system of claim 8 further comprising an optical waveguide modeling system having at least one multicore optical fiber with at least one portion attached to the bone and/or tool, the computer-assisted surgery controller generating a waveguide model representing the multicore optical fiber as attached to the bone and/or tool; and continuously tracking and outputting a second position and/or orientation of the bone and/or tool using the waveguide model.

12. The system of claim 11, wherein the computer-assisted surgery controller is for comparing the first position and/or orientation of the bone and/or tool to the second position and/or orientation of the bone and/or tool.

13. The system of claim 11, wherein the computer-assisted surgery controller is for generating an alert upon determining a difference exceeding a threshold between the first and second positions and/or orientations of the bone and/or tool.

14. The system of claim 8, wherein the at least one electromagnetic sensor is secured to the bone and/or tool via an adhesive.

15. The system of claim 1, further including merging the points with a 3D model of the bone and/or tool.

16. The system of claim 1, wherein registering the geometrical relation of points of a surface of the bone and/or tool relative to the electromagnetic sensor includes registering the points using a registration pointer.

17. The system of claim 1, wherein registering the geometrical relation of points includes a position and orientation of the electromagnetic sensor.

18. The system of claim 1, wherein registering the geometrical relation of points relating the at least one electromagnetic sensor to the bone and/or tool includes registering the geometrical relation of points after receiving said signal.

19. A system for tracking at least one tool relative to a bone in computer-assisted surgery, comprising:

a processing unit; and a non-transitory computer-readable memory communicatively coupled to the processing unit and comprising computer-readable program instructions executable by the processing unit for:

calibrating a surface of a bone and/or tool relative to at least one electromagnetic sensor by registering a fixed geometrical relation of points of the surface of the bone and/or tool relative to the at least one electromagnetic sensor;

continuously emitting an electromagnetic field in a surgical volume incorporating the at least one electromagnetic sensor on the bone and/or tool;

sensing the electromagnetic field with the at least one electromagnetic sensor and continuously receiving a signal indicative of a position and/or orientation of the at least one electromagnetic sensor relative to the emitting of electromagnetic field;

processing the signal to determine the position and/or orientation of the at least one electromagnetic sensor; and continuously tracking and outputting a first position and/or orientation of the bone and/or tool using the geometrical data and the position and/or orientation of the at least one electromagnetic sensor.

* * * * *